US007745486B2

(12) United States Patent
Lines

(10) Patent No.: US 7,745,486 B2
(45) Date of Patent: Jun. 29, 2010

(54) QUERCETIN-CONTAINING COMPOSITIONS

(75) Inventor: Thomas Christian Lines, Wayland, MA (US)

(73) Assignee: Quercegen Pharma LLC, Newton, MA (US)

( * ) Notice: Subject to any disclaimer, the term of this patent is extended or adjusted under 35 U.S.C. 154(b) by 60 days.

(21) Appl. No.: 11/778,234

(22) Filed: Jul. 16, 2007

(65) Prior Publication Data

US 2008/0015247 A1    Jan. 17, 2008

Related U.S. Application Data

(60) Provisional application No. 60/807,601, filed on Jul. 17, 2006, provisional application No. 60/807,694, filed on Jul. 18, 2006, provisional application No. 60/900,626, filed on Feb. 8, 2007, provisional application No. 60/911,747, filed on Apr. 13, 2007, provisional application No. 60/913,164, filed on Apr. 20, 2007.

(51) Int. Cl.
*A61K 31/35* (2006.01)
*A61K 31/44* (2006.01)
*A61K 31/34* (2006.01)

(52) U.S. Cl. ................. 514/457; 514/355; 514/474

(58) Field of Classification Search ................. 514/183, 514/355, 457, 474
See application file for complete search history.

(56) References Cited

U.S. PATENT DOCUMENTS

| | | | |
|---|---|---|---|
| 5,026,721 A | 6/1991 | Dudrick et al. | |
| 5,804,594 A | 9/1998 | Murad | |
| 5,846,569 A | 12/1998 | Anderson et al. | |
| 5,948,443 A | 9/1999 | Riley et al. | |
| 6,103,756 A | 8/2000 | Gorsek | |
| 6,203,818 B1 | 3/2001 | Vester | |
| 6,210,701 B1 | 4/2001 | Darland et al. | |
| 6,261,589 B1 | 7/2001 | Pearson et al. | |
| 6,277,426 B1 | 8/2001 | Reust | |
| 6,277,427 B1 | 8/2001 | Husz | |
| 6,299,925 B1 | 10/2001 | Xiong et al. | |
| 6,352,712 B1 * | 3/2002 | Lukaczer et al. | 424/439 |
| 6,491,948 B1 | 12/2002 | Buchholz et al. | |
| 6,511,675 B2 | 1/2003 | Siddiqui et al. | |
| 6,551,629 B1 | 4/2003 | Gorsek | |
| 6,579,544 B1 | 6/2003 | Rosenberg et al. | |
| 6,821,536 B2 | 11/2004 | Lines et al. | |
| 7,041,652 B1 | 5/2006 | Buchholz et al. | |
| 7,270,840 B2 | 9/2007 | Lines et al. | |
| 2002/0025350 A1 | 2/2002 | Siddiqui et al. | |
| 2002/0151599 A1 | 10/2002 | Buchholz et al. | |
| 2003/0054357 A1 | 3/2003 | Young et al. | |
| 2003/0068391 A1 | 4/2003 | Harris et al. | |
| 2004/0101595 A1 | 5/2004 | Lines et al. | |
| 2004/0126461 A1 | 7/2004 | Lines et al. | |
| 2005/0031737 A1 | 2/2005 | Lines et al. | |
| 2005/0266121 A1 | 12/2005 | Lines et al. | |
| 2007/0148210 A1 | 6/2007 | Lines et al. | |

FOREIGN PATENT DOCUMENTS

| | | |
|---|---|---|
| WO | WO 9841195 A2 * | 9/1998 |
| WO | WO 00/12085 | 3/2000 |
| WO | WO 02/07768 | 1/2002 |

OTHER PUBLICATIONS

Bors et al., "Flavanoids and Polyphenols: Chemistry and Biology," *Handbook of Antioxidants*, pp. 409-416 (1996).
Chow et al., "Phase I Pharmacokinetic Study of Tea Polyphenols Following Single-dose Administration of Epigallocatechin Gallate and Polyphenon E," Cancer Epidemiology, Biomarkers & Prevention 10:53-58 (2001) XP-002366662.
Crespy et al., "Quercetin, but not Its Glycosides, Is Absorbed from the Rat Stomach," Journal of Agricultural and Food Chemistry, vol. 50, pp. 68-621 (2002).
Dequan et al., "Survey of Bioflavonoids," Food and Fermentation Industries, 25(16): 52-56 (1999) (Translation of English Abstract).
Erlund et al., "Pharmacokinetics of Quercetin from Quercetin Aglycone and Rutin in Healthy Volunteers," Eur. J. Clin. Pharmacol., 56:545-553 (2000).
Guardia et al., "Anti-Inflammatory Properties of Plant Flavinoids. Effect of Rutin, Quercetin and Hesperidin on Adjuvant Arthritis in Rat," Il Farmaco, 56: 683-687 (2001).
Koo et al., "Pharmacological Effects of Green Tea on the Gastrointestinal System," European Journal of Pharmacology 500:177-184 (2004).
Min et al., "The Chemistry and Medical Application of Tea Polyphenol," Hubei Chemical Industry, 2001, 3, 29-31 (Translation of English Abstract).
Saucier et al., "Synergetic Activity of Catechin and Other Antioxidants," Journal of Agricultural and Food Chemistry, 47(11): 4491-4494 (1999).
Sesink et al., "Quercetin Glucuronides but Not Glucosides Are Present in Human Plasma After Consumption of Quercetin-3-Glucoside or Quercetin-4-Glucoside," Human Nutrition and Metabolism Research Communication, pp. 1938-1941 (2001).
Thomas et al., "Ascorbate and Phenolic Antioxidant Interations in Prevention of Liposomal Oxidation," Lipids 27(7) (1992).
Walle et al., "Quercetin Glucosides Are Completely Hydrolyzed in Ileostomy Patients before Absorption," Human Nutrition and Metabolism Research Communication, pp. 2658-2661 (2000).
Label distributed with FRS products, Delivery Receipt bearing date Jul. 19, 2005.
Label distributed with FRS products, Delivery Receipt bearing date Aug. 11, 2004.

* cited by examiner

*Primary Examiner*—Kevin Weddington
(74) *Attorney, Agent, or Firm*—Occhiuti Rohlicek & Tsao LLP

(57) ABSTRACT

This invention relates to a composition containing quercetin, vitamin B3, and vitamin C. Also disclosed is a method of using the composition for enhancing physical or mental performance or treating various diseases or disorders.

26 Claims, No Drawings

QUERCETIN-CONTAINING COMPOSITIONS

CROSS-REFERENCE TO RELATED APPLICATIONS

This application claims priority from U.S. Provisional Patent Application No. 60/807,601, filed Jul. 17, 2006, U.S. Provisional Patent Application No. 60/807,694, filed Jul. 18, 2006, U.S. Provisional Patent Application No. 60/900,626, filed Feb. 8, 2007, U.S. Provisional Patent Application No. 60/911,747, filed Apr. 13, 2007, and U.S. Provisional Patent Application No. 60/913,164, filed Apr. 20, 2007. Contents of these prior applications are incorporated herein by reference in their entireties.

BACKGROUND

It is known that certain natural antioxidants, such as quercetin, inhibit both acute and chronic phases of free-radical induced diseases. Further, some natural antioxidants exhibit synergy in their reactions with biologically relevant oxygen species, e.g., hydroxyl radicals, superoxides, oxysulfurs, sulfur dioxide, and nitrogen dioxide.

SUMMARY

In one aspect, the invention features a composition containing quercetin, vitamin B3, and vitamin C, in which a weight ratio between quercetin, vitamin B3, and vitamin C is 1:0.02-1:0.2-2.5.

The composition, either in dry form (e.g., powder or tablet) or in liquid form (e.g., beverage or syrup), can be a dietary supplement or a pharmaceutical formulation. The dietary supplement or the pharmaceutical formulation can be in the form of a tablet, a capsule, a soft chew, or a gel. The composition can also be a food product. Examples include tea (e.g., a tea drink and the contents of a tea bag), soft drinks, juice (e.g., a fruit extract and a juice drink), milk, coffee, jelly, ice cream, yogurt, cookies, cereals, chocolates, and snack bars.

In another aspect, the invention features a composition consisting essentially of quercetin, vitamin B3, and vitamin C. The term "consisting essentially of" used herein limits the composition to the just-mentioned three ingredients and those that do not materially affect its basic and novel characteristics, i.e., the efficacy in treating one or more target conditions described herein (e.g., mental fatigue, viral infection, and tumor). An example of such a composition contains the just-mentioned three ingredients and a pharmaceutically acceptable carrier. Another example is a soft chew composition containing the three ingredients and various inactive additives (e.g., excipients, sweeteners, and artificial flavors).

In still another aspect, the invention features a method for enhancing physical or mental performance. The method includes administering to a subject in need thereof an effective amount of the above-described composition. Examples of improved physical performance include increased stamina and improved speed, strength, power, endurance, flexibility, agility, balance, focus coordination, reaction time, and fatigue recovery. Examples of improved mental performance include improved sharpness, attention span, mental alertness, cognitive functions, and/or mood elevation, and recovery or reduction of depression, anxiety, and/or mental fatigue (e.g., following a high-intensity physical exercise). By properly administrating the composition, a subject's physical or mental performance can be greatly enhanced without deleterious side effects.

In yet another aspect, the invention features a method for treating a disorder associated with C-reactive protein (e.g., a cardiovascular disorder) or lowering cholesterol levels by administering to a subject in need thereof an effective amount of the above-described composition.

In a further aspect, the invention features a method of administering to a subject in need thereof an effective amount of the above-described composition to treat one or more of the following diseases: autoimmune disease, inflammatory disease, arthritis, tumor, diabetes, sexual dysfunction, chronic constipation, cold, viral and bacterial infection (e.g., upper respiratory tract infection), or neurodegenerative disease (e.g., age-related brain degenerative disease).

Also within the scope of this invention is a composition containing the composition described above for use in treating the above-described disorders or conditions, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

This invention is based, at least in part, on the unexpected findings that a composition containing quercetin, vitamin B3, and vitamin C as active ingredients exhibits synergistic health benefits, including enhancing physical or mental performance in a subject, and that, upon oral administration, a combination of quercetin, vitamin B3, and vitamin C results in a significantly higher quercetin concentration in plasma than quercetin alone. Additional and related surprising observations include that a combination of quercetin, vitamin B3, and vitamin C maintains quercetin levels in plasma up to five times those of quercetin alone or a combination of quercetin and vitamin B3; and that a combination of quercetin, vitamin B3, and vitamin C results in a quercetin half life in plasma twice as long as that of quercetin alone and about one and a half times that of a combination of quercetin and vitamin B3.

The weight ratio between quercetin, vitamin B3, and vitamin C in a composition of the invention can be 1:0.02-1:0.2-2.5, or any ratio in between. For example, the weight ratio can be 1:0.04-0.5:0.3-2.0, 1:0.05-0.3:0.4-1.5, 1:0.05-0.2:0.5-1, and 1:0.1-0.2:0.5-1. Preferred ratios include about 1:0.02:1, about 1:0.04:1, about 1:0.08:1, about 1:0.05:1.5, and about 1:0.16:1. Typically, a subject can be administered, once or periodically per day, with the composition in an amount that provides 100 mg to 2 g (preferably, 250 mg to 1 g) of quercetin. The term "quercetin" refers to both quercetin aglycon and quercetin derivatives, e.g., quercetin-3-O-glucoside, quercetin-5-O-glucoside, quercetin-7-O-glucoside, quercetin-9-O-glucoside, quercetin-3-O-rutinoside, quercetin-3-O-[α-rhamnosyl-(1→2)-α-rhamnosyl-(1→6)]-β-glucoside, quercetin-3-O-galactoside, quercetin-7-O-galactoside, quercetin-3-O-rhamnoside, and quercetin-7-O-galactoside. After digestion, quercetin derivatives are converted to quercetin aglycon and other active derivatives, which are absorbed in the body. The quantity of quercetin mentioned above refers to that of quercetin aglycon or the quercetin moiety of a quercetin derivative. Quercetin can be added to the composition either in a pure form or as an ingredient in a mixture (e.g., a plant extract). Examples of commercially available quercetin include QU995 (containing 99.5% quercetin) and QU985 (containing 98.5% quercetin) from Quercegen Pharma LLC (Newton, Mass.) and Merck KGaA (Brazil). "Vitamin B3" mentioned herein includes vitamin B3 in its various forms, including niacinamide, nicotinic acid, nicotinamide, inositol hexaniacinate. "Vitamin C" mentioned herein includes vitamin C (i.e., L-ascorbic acid, D-ascorbic acid, or both) and its salts (e.g., sodium ascorbate).

The composition of this invention can be in various forms. For example, it can be a soft chew composition that includes quercetin, niacinamide, ascorbic acid, sodium ascorbate, sugar, corn syrup, sucralose, soy lecithin, corn starch, glycerin, palm oil, xylitol, carrageenan, FD&C Yellow #6, FD&C Yellow #5, and natural and/or artificial flavors. An exemplary serving of this soft chew composition (5.15 g) includes 250 mg of quercetin, 12.9 mg of vitamin B3 (i.e., niacinamide), and 382.8 mg vitamin C (i.e., L-ascorbic acid and sodium ascorbate). A subject can take one to eight servings (e.g., 4 servings) of this soft chew composition daily. The amounts taken can vary depending on, for example, the disorder or condition to be treated and the physical states of the subject. Another exemplary composition of this soft chew includes 5.25 wt % of quercetin, 0.25 wt % of vitamin B3, and 7.81 wt % of vitamin C (i.e., L-ascorbic acid and sodium ascorbate).

The composition of this invention can further contain one or more active ingredients, such as an isoflavone (e.g., genistein or genistin), curcumin, resveratrol, isoquercetin, luteolin, epigallocatechin gallate (EGCG), CoQ10, eicosapentaenoic acid (EPA), and docosahexaenoic acid (DHA). These active ingredients can be added to the composition either in a pure form or as a component in a mixture (e.g., an extract from a plant or an animal). A suitable daily dosage of each of these ingredients can vary depending on, for example, the disorder or condition to be treated and the physical states of the subjects. Exemplary daily dosages of some of these ingredients are: 20-2,500 mg (preferably 250-1,000 mg) of curcumin, 10-1,000 mg (preferably 100-500 mg) of resveratrol, 10-1,000 mg (preferably 100-250 mg) of isoquercetin, 50-1,000 mg (preferably 100-700 mg) of EGCG, 25-300 mg (preferably 50-100 mg) of genistin/genistein, 10-1,000 mg (preferably 100-200 mg) of luteolin, 50-1,000 mg (preferably 70-500 mg) of EPA, and 50-1,000 mg (preferably 80-700 mg) of DHA. Further, it can be sweetened, if necessary, by adding a sweetener such as sorbitol, maltitol, hydrogenated glucose syrup and hydrogenated starch hydrolyzate, high fructose corn syrup, cane sugar, beet sugar, pectin, and sucralose. The composition can also contain amino acids, fatty acids, proteins, fibers, minerals, a flavor enhancer, or a coloring agent. Exemplary amino acids include theanine (e.g., L-theanine) and alanine (e.g., L-alanine). Exemplary fatty acids include omega-3 fatty acids (e.g., linolenic acid), omega-6 fatty acids (e.g., linoleic acid), and omega-9 fatty acids (e.g., oleic acid). Exemplary proteins include plant proteins, such as soy proteins and chia seed proteins. Exemplary fibers include plant fibers, such as soy fibers and chia seed fibers. These ingredients can be added in the above-described composition either in a pure form or as a component in a mixture (e.g., an extract from a plant or an animal).

When the above-described composition is in powder form, it can be used conveniently to prepare beverage, paste, jelly, capsules, or tablets. Lactose and corn starch are commonly used as diluents for capsules and as carriers for tablets. Lubricating agents, such as magnesium stearate, are typically included in tablets.

The composition of this invention can be a dietary supplement or a pharmaceutical formulation. As a dietary supplement, additional nutrients, such as minerals or amino acids may be included. The composition can also be a food product. As used herein, the term "food" broadly refers to any kinds of liquid and solid/semi-solid materials that are used for nourishing humans and animals, for sustaining normal or accelerated growth, or for maintaining stamina or alertness. Examples of human food products include, but are not limited to, tea-based beverages, juice, coffee, milk, jelly, cookies, cereals, chocolates, snack bars, herbal extracts, dairy products (e.g., ice cream, and yogurt), soy bean product (e.g., tofu), and rice products.

The composition of this invention significantly lowers both cholesterol and C-reactive protein levels, and increases the hemoglobin levels, the number of reticulocytes, and the mass of red blood cells. For example, it lowers the C-reactive protein levels in both subjects having higher than normal C-reactive protein levels and subjects having normal C-reactive protein levels. Further, this composition results in increased mitochondrial biogenesis or retention (e.g., in muscle and brain cells), reduced mitochondrial DNA damage and loss of mitochondria, or increased cytochrome C levels and citrate synthase activities. Thus, it is useful in treating disease associated with mitochondrial deficiencies in both humans and animals. This composition can also induce gene expression and activity of T-helper lymphocyte (Th-1) cytokines (e.g., interferon gamma) and can down-regulate T-helper lymphocyte 2 (Th-2) cytokines (e.g., interleukin 13). In addition, it can inhibit the expression and/or activity of one or more of the following three enzymes: matrix metalloproteinase 1 (MMP1), matrix metalloproteinase 2 (MMP2), and cyclooxygenase 2 (COX2). It can also block pathways mediated by epidermal growth factor receptor, such as epiregulin-mediated pathways. This composition can be used for enhancing or maintaining physical or mental performance, reducing infection in physically stressed athletes or non-athletes, and improving immune system recovery from intense physical exercises. It also can be an activator of Sirtuin.

This composition can also be used for treating diseases or disorders, such as a disorder associated with C-reactive protein, autoimmune disease (e.g., multiple sclerosis, thyroiditis, rheumatoid arthritis, myositis, lupus, or Celiac disease), skin disease (e.g., eczema, urticaria, or psoriasis), lung disease (asthma, pulmonary fibrosis, or chronic obstructive pulmonary disease), prostatitis, arthritis, tumor, diabetes (type II diabetes), sexual dysfunction, chronic constipation, inflammatory disease (e.g., inflammatory bowel disease such as Crohn's disease or ulcerative colitis), infection, neurodegenerative disease (e.g., dyslexia, dyspraxia, autism, Asperger's disease, Alzheimer's disease, and mild cognitive impairment), and developmental disorder (e.g., attention deficit disorder or attention deficit hyperactivity disorder); for treating brain injury (e.g., physical damages to the brain); for improving concentration or mood; for improving the immune system, and for lowering blood cholesterol levels or blood pressure. "A disorder associated with C-reactive protein" refers to any disorder that results in an increase in the number of C-reactive protein in blood, such as inflammation or a cardiovascular disorder (e.g., atherosclerosis, coronary heart disease, stroke, and peripheral arterial disease). "Tumor" refers to both benign tumor and malignant tumor (e.g., leukemia, colon cancer, prostate cancer, kidney cancer, liver cancer, breast cancer, or lung cancer). "Infection" includes viral, bacterial, parasitic, and other microbial infection. Examples of viral infection treatable by this composition include influenza (e.g., Avian influenza or infection with influenza A virus subtype H5N1), severe acute respiratory syndrome (SARS), human immunodeficiency virus (HIV) infection, herpes simplex virus infection, respiratory syncytial virus (RSV) infection, rhinovirus (e.g., human rhinovirus) infection, and coronavirus infection. The mechanism for treating viral infection by this composition can include early stage inhibition of viral reproduction by reduction of viral RNA or DNA (e.g., by inhibition of transcription, reverse transcription, and translation). Bacterial infection include infection by either gram+ or gram− bacteria and infection by either anaerobic or aerobic bacteria. Examples of parasitic infection include leishmaniasis, malaria, and trypanosoma. Other examples of infection include respiratory infection, digestive tract infection, urinary tract infection, blood infection, and nervous system infection.

Further, this composition can be used to treat certain symptoms of the above-mentioned diseases or disorders. For example, it can be used to lessen certain symptoms of multiple sclerosis, including muscle weakness, wasting of muscles, pain (such as facial pain or pain without apparent cause), electrical shock sensation, loss of awareness of location of body parts, loss of coordination (such as in speech), shaking when performing fine movements, loss of ability to produce rapidly alternating movement (e.g., movement in a rhythm), and short-term or long term memory loss. As another example, it can be used to reduce the incidence, severity, and/or duration of cold and flu symptoms. In addition, this composition can also be used as a dietary supplement to improve the quality of life of a patient. For example, it can be used to reduce obesity (e.g., as a part a weight management plan), slow the aging process, enhance innate immunity, and improve skin health, sexual performance, and digestion.

In addition, this composition can be used to lessen negative side effects caused by chemotherapy with drugs such as glivec, taxol, and tamoxifen. It also can be used as an energy booster for patients in need thereof, e.g., cancer patients or AIDS patients. Moreover, it is useful in enhancing athletic performance for both humans and animals, e.g., horses.

The terms "improving," "enhancing," "treating," and "lowering" refer to the administration of an effective amount of a composition of the invention to a subject, who needs to improve one or more of the above-mentioned conditions or has one or more of the just-mentioned disorders, or a symptom or a predisposition of one of more of the disorders or conditions, with the purpose to improve one or more of these conditions, or to prevent, cure, alleviate, relieve, remedy, or ameliorate one or more of these disorders, or the symptoms or the predispositions of one or more of them. The term "administration" covers oral or parenteral delivery to a subject a composition of the invention in any suitable form, e.g., food product, beverage, tablet, capsule, suspension, and solution. The term "parenteral" refers to subcutaneous, intracutaneous, intravenous, intramuscular, intraarticular, intraarterial, intrasynovial, intrasternal, intrathecal, intralesional, and intracranial injection, as well as various infusion techniques. An "effective amount" refers to a dose of the composition that is sufficient to provide a physical benefit (e.g., improving endurance) or a therapeutic benefit (e.g., lowering cholesterol or C-reactive protein levels, or reducing the risk of atherosclerosis or heart diseases). Both in vivo and in vitro studies can be conducted to determine optimal administration routes and doses.

The compositions described above can be preliminarily screened for their efficacy in treating the above-described conditions by in vitro assays and then confirmed by animal experiments and clinic trials. Other suitable analytical and biological assays are apparent to those of ordinary skill in the art. For example, the bioavailability of quercetin can be measured by conducting pharmacokinetic studies and evaluated by the area under the curve in a plasma-drug concentration time curve.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A composition comprising quercetin, vitamin B3, and vitamin C as the only active ingredients, wherein a weight ratio between the quercetin, the vitamin B3, and the vitamin C is 1:0.02-1:0.2-2.5.

2. The composition of claim 1, wherein the weight ratio is 1:0.05-0.2:0.5-1.

3. The composition of claim 1, wherein the weight ratio is 1:0.1-0.2:0.5-1.

4. The composition of claim 1, wherein the weight ratio is 1:0.04:1.

5. The composition of claim 1, wherein the weight ratio is 1:0.08:1.

6. The composition of claim 1, wherein the composition is in dry form.

7. The composition of claim 1, wherein the composition is in liquid form.

8. The composition of claim 1, wherein the composition is a food product selected from the group consisting of tea, soft drink, juice, milk, coffee, jelly, ice cream, yogurt, cookie, cereal, chocolate, and snack bar.

9. The composition of claim 8, wherein the food product is tea, soft drink, juice, or snack bar.

10. The composition of claim 1, wherein the composition is a dietary supplement or a pharmaceutical formulation.

11. The composition of claim 10, wherein the composition is a tablet, a capsule, a soft chew, or a gel.

12. The composition of claim 1, wherein the vitamin B3 is niacinamide.

13. The composition of claim 1, wherein the vitamin B3 is nicotinic acid.

14. A composition comprising quercetin, vitamin B3, vitamin C, and another agent as the only active ingredients, wherein a weight ratio between the quercetin, the vitamin B3, and the vitamin C is 1:0.02-1:0.2-2.5, and the other agent is selected from the group consisting of genistein, genistin, curcumin, reserveratrol, isoquercetin, epigallocatechin gallate (EGCG), eicosapentaenoic acid (EPA), docosahexaenoic acid (DHA), and a combination thereof.

15. The composition of claim 14, wherein the other agent is a combination of isoquercetin, EGCG, EPA, and DHA.

16. The composition of claim 14, wherein the weight ratio is 1:0.05-0.2:0.5-1.

17. The composition of claim 14, wherein the weight ratio is 1:0.1-0.2:0.5-1.

18. The composition of claim 14, wherein the weight ratio is 1:0.04:1.

19. The composition of claim 14, wherein the weight ratio is 1:0.08:1.

20. The composition of claim 14, wherein the composition is in dry form.

21. The composition of claim 14, wherein the composition is in liquid form.

22. The composition of claim 14, wherein the composition is a food product selected from the group consisting of tea, soft drink, juice, milk, coffee, jelly, ice cream, yogurt, cookie, cereal, chocolate, and snack bar.

23. The composition of claim 14, wherein the vitamin B3 is niacinamide.

24. The composition of claim 14, wherein the vitamin B3 is nicotinic acid.

25. The composition of claim 14, wherein the composition is a dietary supplement or a pharmaceutical formulation.

26. The composition of claim 25, wherein the composition is a tablet, a capsule, a soft chew, or a gel.

* * * * *